United States Patent [19]
Lowery et al.

[11] Patent Number: 5,364,345
[45] Date of Patent: Nov. 15, 1994

[54] METHOD OF TUBAL RECANALIZATION AND CATHETER SYSTEM THEREFOR

[75] Inventors: Guy R. Lowery, Mission Viego; Steven R. Bacich, Laguna Niguel; Keith Tholin, Irvine, all of Calif.

[73] Assignee: Imagyn Medical, Inc., Laguna Niguel, Calif.

[21] Appl. No.: 53,152

[22] Filed: Apr. 26, 1993

Related U.S. Application Data

[63] Continuation-in-part of Ser. No. 780,871, Oct. 18, 1991, abandoned.

[51] Int. Cl.$^5$ ............... A61B 1/00; A61M 31/00
[52] U.S. Cl. ...................... 604/49; 604/55; 128/4
[58] Field of Search .................. 604/49–55, 604/264, 271; 128/4

[56] References Cited

U.S. PATENT DOCUMENTS

| | | |
|---|---|---|
| 4,033,331 | 7/1977 | Guss et al. |
| 4,160,446 | 7/1974 | Barrington |
| 4,243,040 | 1/1981 | Beecher |
| 4,271,839 | 6/1981 | Fogarty et al. |
| 4,321,915 | 3/1982 | Leighton et al. ............. 128/4 |
| 4,437,857 | 3/1984 | Goldstein et al. |
| 4,479,497 | 10/1984 | Fogarty et al. |
| 4,493,711 | 1/1985 | Chin et al. |
| 4,526,175 | 7/1985 | Chin et al. |
| 4,530,698 | 7/1985 | Goldstein et al. |
| 4,604,094 | 8/1986 | Shook |
| 4,606,347 | 8/1986 | Fogarty |
| 4,946,440 | 8/1990 | Hall ..................... 604/95 |
| 5,108,366 | 4/1992 | Schatz |
| 5,163,927 | 11/1992 | Woker et al. |
| 5,171,305 | 12/1992 | Schickling et al. |
| 5,236,423 | 8/1993 | Mix et al. ............... 604/271 |
| 5,259,364 | 11/1993 | Bob et al. ............... 128/4 |

FOREIGN PATENT DOCUMENTS

| | | |
|---|---|---|
| 2406823 | 8/1875 | Germany |
| 2823025 | 12/1979 | Germany |
| WO8001353 | 7/1980 | WIPO |
| WO9101677 | 2/1991 | WIPO |

OTHER PUBLICATIONS

"A Miniature Toposcopic Catheter Suitable for Small Diameter Tortuous Blood Vessels", Goldstein et al., Transactions of the ASME Journal of Biomechanical Engineering, vol. 102, Aug. 1980, No. 3, pp. 221–229.
"Topo Pathfinder Catheters", Houston Biomedical, Inc., TPC/15M/1087/AW.
"Everting (Toposcopic) Catheter for Broad Clinical Application", D. R. Shook et al., Transactions of the ASME, vol. 109, May 1986, pp. 168, 170, 172–174.
"The Ins and Outs of Toposcopy and the Everting Catheter", D. R. Shook, SOMA, (Jul. 1987), pp. 22–27.
"Transcervical Intra Fallopian Endoscopy–Falloposcopy", Focus on Reproduction, Jan. 1993, Bauer et al.
"Nonoperative Embryo Transfer to the Fallopian Tube", Jansen et al., The New England Journal of Medicine, pp. 288–290, Aug. 4, 1988.
"Retrograde tubular transfer of human embryos", Risquez et al., Human Reproduction, pp. 185–188, 1990.
"Gemete intrafallopian transfer by hysteroscopy as an alternative treatment for infertility", Possati et al., Fertility and Sterility, vol. 56, No. 3, Sep. 1991, pp. 496–499.
"Transcervical access and intra-luminal imaging of the Fallopian tube in the non-anaesthetized patient; Preliminary results using a new technique for Fallopian access", Otmar Bauer et al., Human Reproduction, vol. 7, Suppl. 1, pp. 7–11, 1992.
"The linear everting catheter: a nonhysteroscopic, transvaginal technique for access and microendoscopy of the fallopian tube", Pearlstone et al., Fertility and Sterility, vol. 68, No. 4, Oct. 1992.

*Primary Examiner*—John D. Yasko
*Assistant Examiner*—Adam J. Cermak
*Attorney, Agent, or Firm*—Gordan L. Peterson

[57] ABSTRACT

A method of tubal recanalization comprising advancing an everting catheter adapted for dilatation and an endoscope to a position adjacent the site of a stenosis in an internal tubal passage of a patient. The everting catheter includes an endoscope lumen and the endoscope is within the endoscope lumen. The everting element is everted to a location within the stenosis and is then expanded to reduce the stenosis. When the tubal passage has been opened sufficiently, the everting element is retracted. The site of the stenosis is viewed using the endoscope and such viewing may be carried out prior to expansion of the everting element to locate the site as well as after the everting element has been retracted.

20 Claims, 4 Drawing Sheets

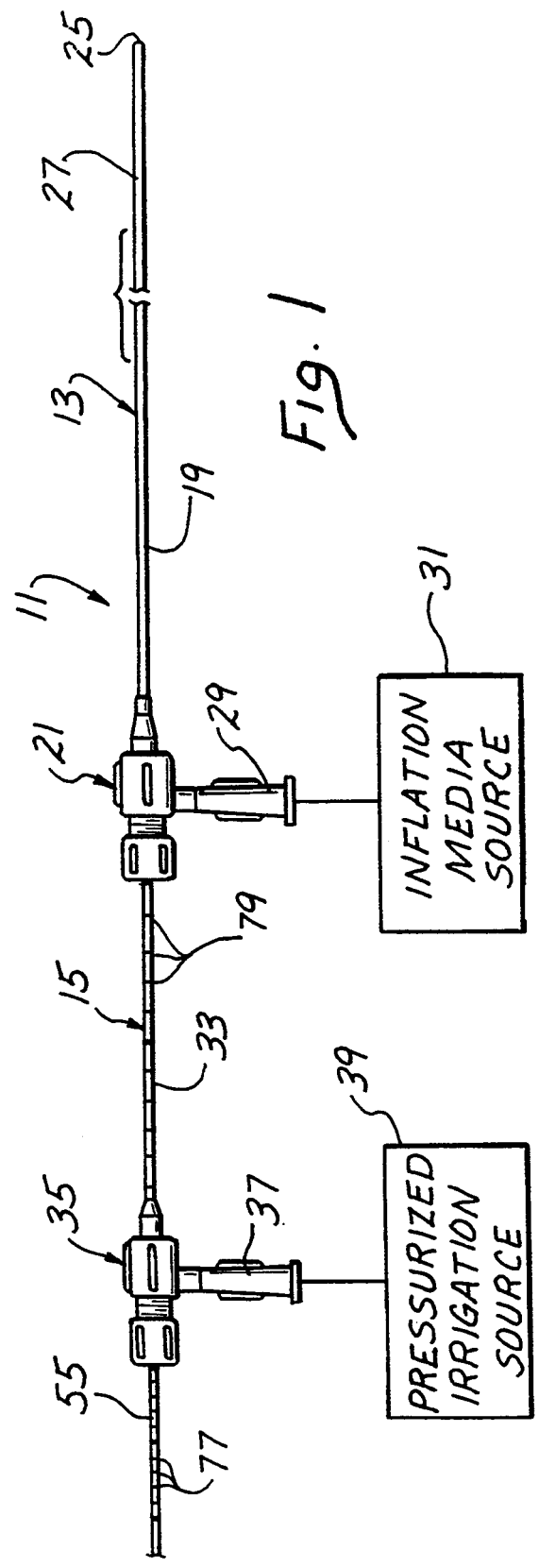
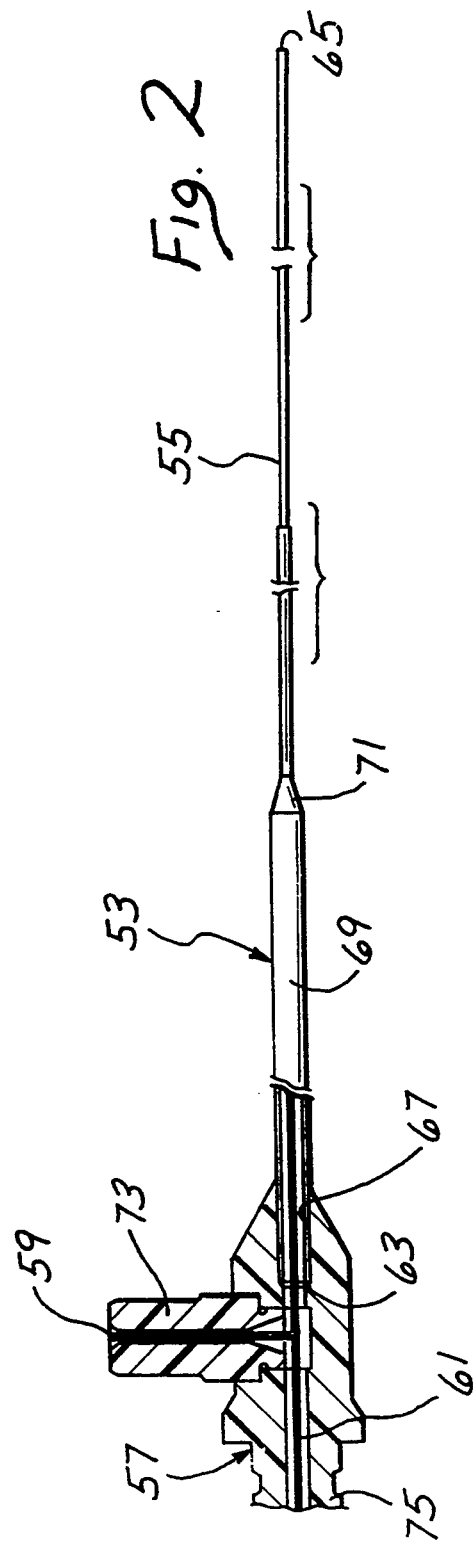

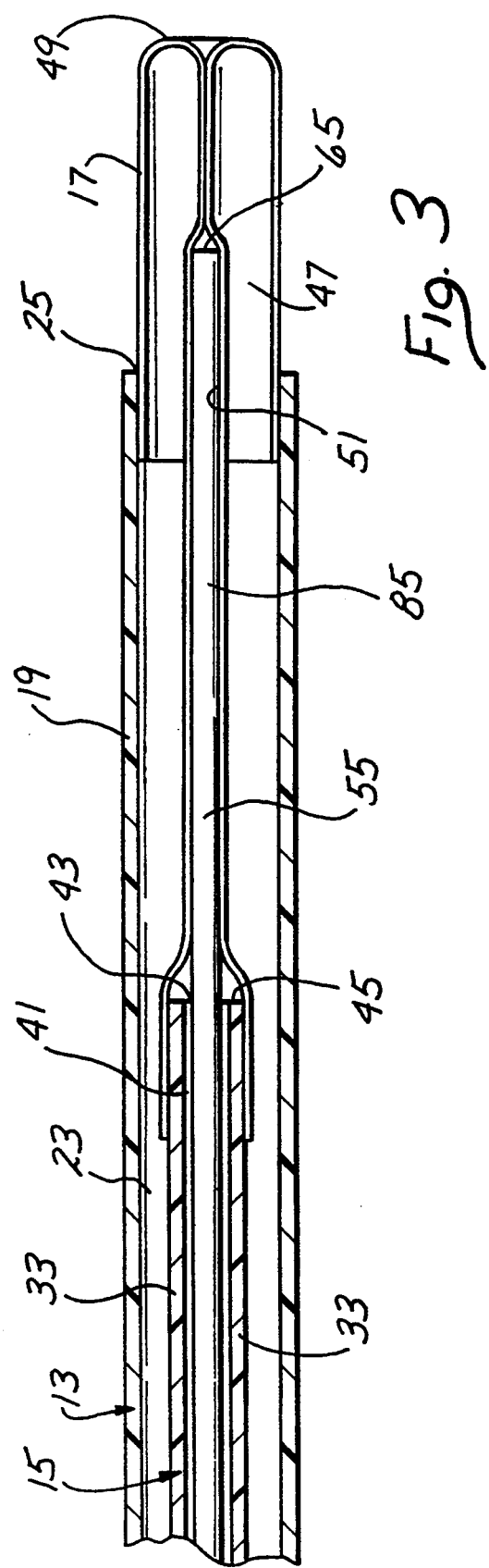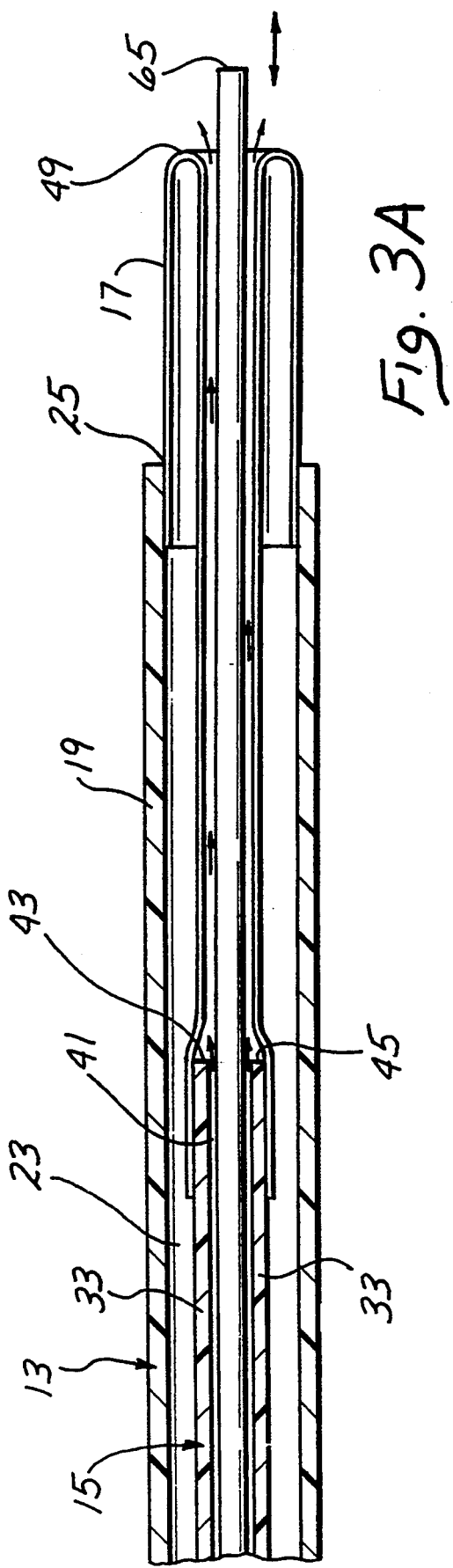

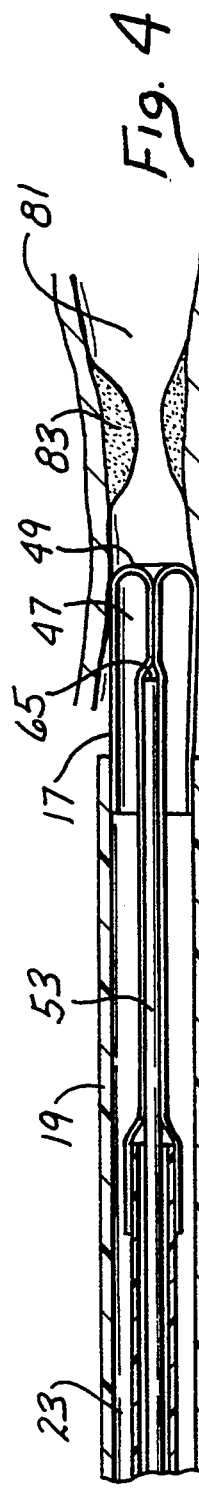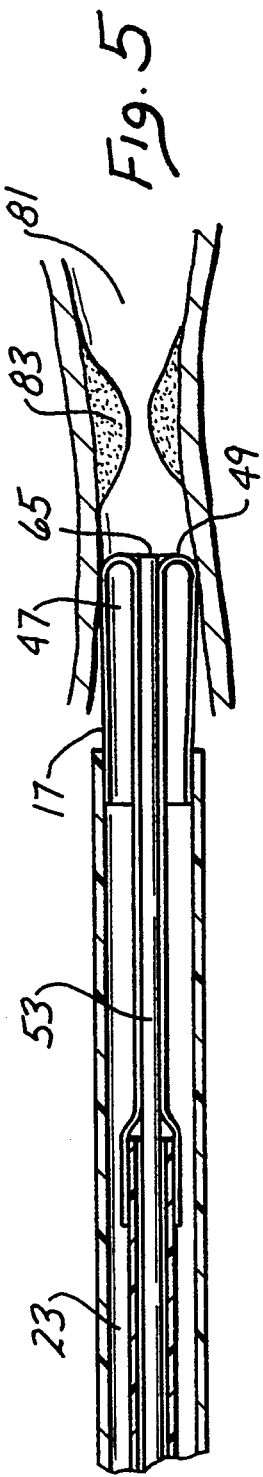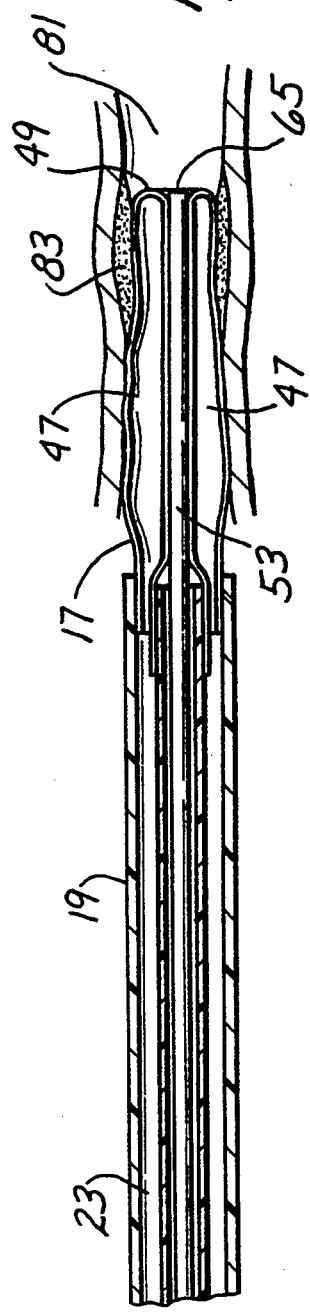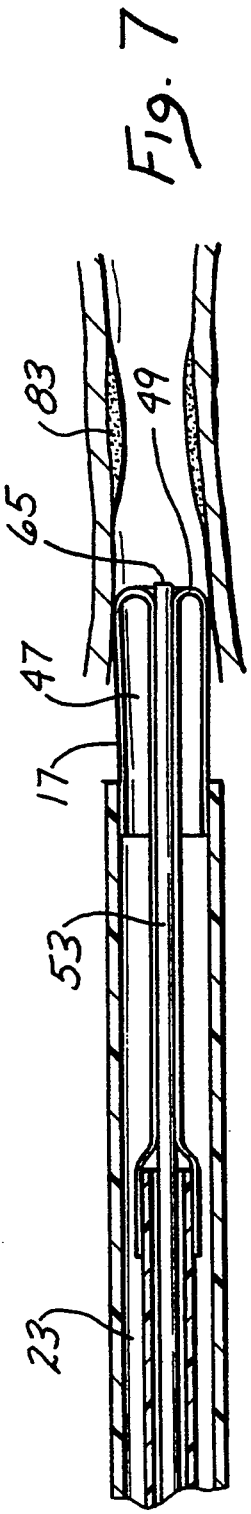

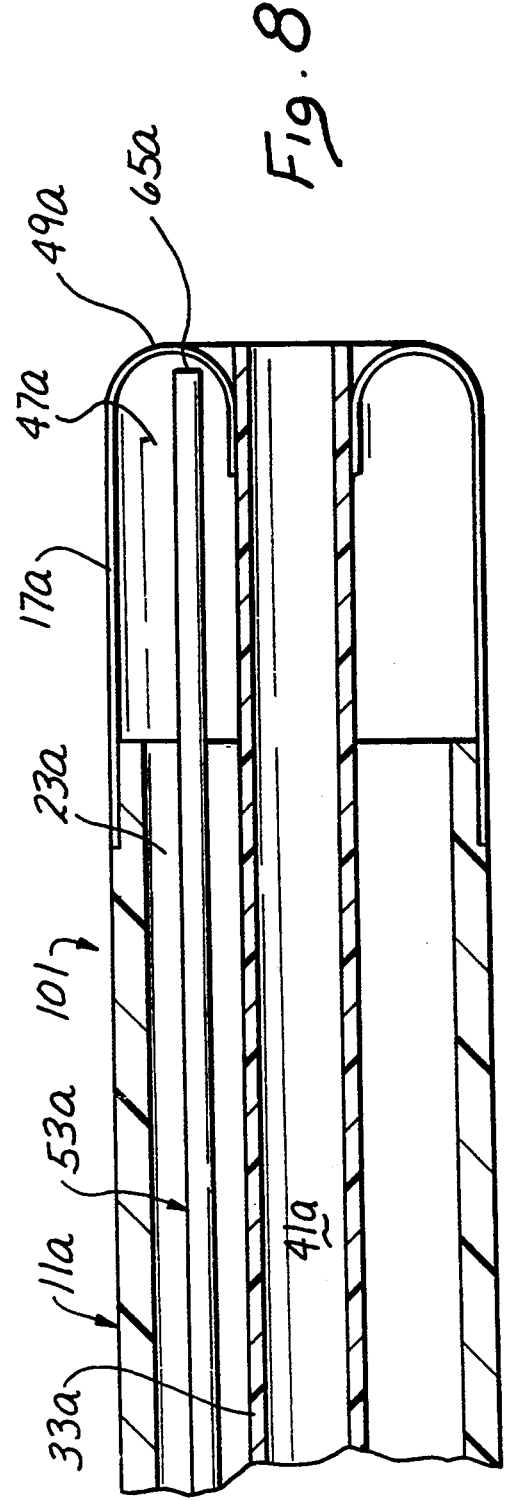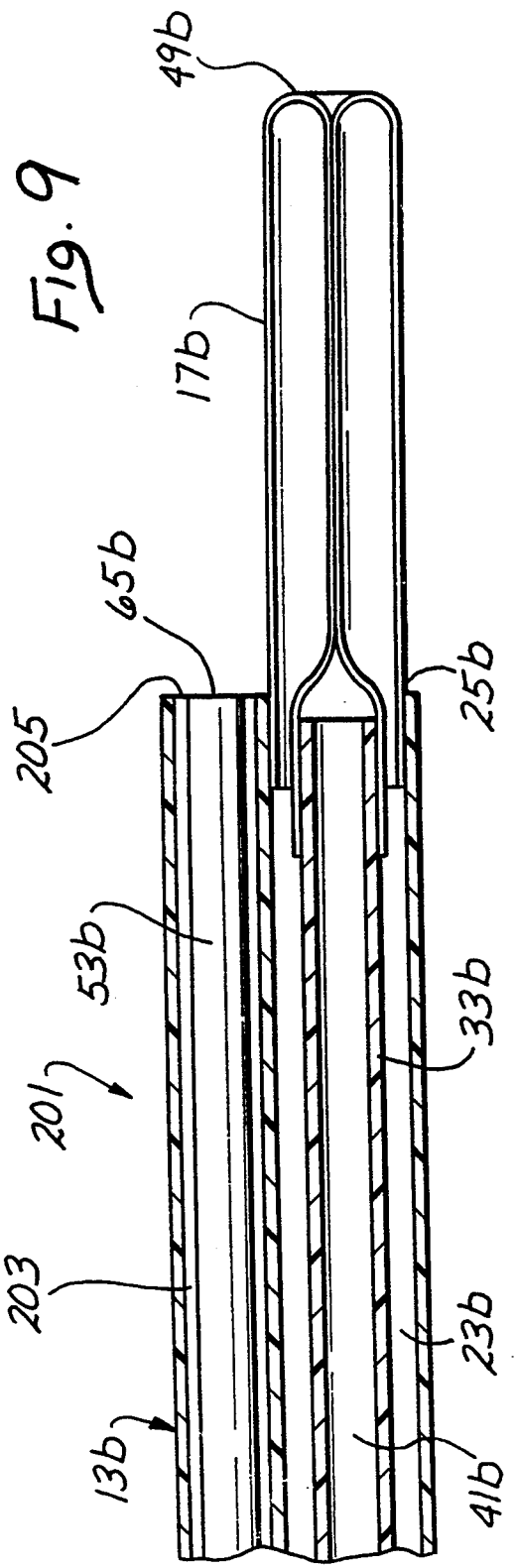

METHOD OF TUBAL RECANALIZATION AND CATHETER SYSTEM THEREFOR

This application is a continuation-in-part of application Ser. No. 780,871 filed on Oct. 18, 1991 and entitled Apparatus and Method for Independent Movement of an Instrument Within a Linear Eversion Catheter (now abandoned).

BACKGROUND OF THE INVENTION

Various internal tubal passages of a patient are subject to being totally or partially occluded by a stenosis. Examples of internal tubal passages which are subject to occlusion or partial occlusion are arteries, fallopian tubes, the cervical canal, biliary duct, pancreatic duct, ureter, urethra, eustachian tube and lactiferous ducts. When occlusion or partial occlusion of an internal tubal passage occurs, it is typically necessary or desirable to remove or partially remove the stenosis to recanalize the tubal passage.

There are a variety of known techniques to achieve tubal recanalization and these includes, for example, Dottering techniques using wires, hydro-irrigation using pressurized fluid sources and coaxial balloon catheters of the type used in balloon angioplasty. An everting catheter can also be designed as a dilatation catheter and in this event, an everting element of the everting catheter is expanded against the stenosis to reduce the stenosis. A catheter of this type is shown and described in Fogarty et al U.S. Pat. No. 4,271,839.

One problem with tubal recanalization procedures is that, so far as we are aware, there are no direct techniques to evaluate the site of the stenosis during and following the recanalization procedure. Indirect evaluations as to the severity of the stenosis can be ascertained from the magnitude of force required to cross and dilate the stenosis. Also, information can be obtained before, during and after the procedure from contrast dye injections. However, none of these procedures provide all of the information desired. In addition the use of contrast dye injections requires exposing the effected region of the patient to X-rays and this is undesirable in certain locations of the body such as the sensitive reproduction tracts of females and males.

Certain endoscopic evaluation techniques are also known. One such technique includes utilizing a balloon to position an angioscope within a central lumen of a catheter. The balloon, however, occludes the blood vessel and obscures the imaging field. Angioscopy used during balloon angioplasty provides both pre and post operative analysis. Thus, angioscopy affords the advantage of direct viewing, but is subject to a somewhat obscure imaging field and blockage of the artery.

It is also known to use an everting catheter to deliver an endoscope to an internal region of a patient such as into the fallopian tubes to visually evaluate such region. However, so far as we are aware this has not been done with an everting catheter which can also treat the stenosis.

SUMMARY OF THE INVENTION

This invention overcomes the problems described above. With this invention, the site of the stenosis can be viewed with an endoscope and the apparatus used for delivering and positioning of the endoscope does not obscure the imaging field. In addition, the apparatus utilized for delivery and positioning of the endoscope is also used for dilatation to reduce the stenosis.

The method of this invention utilizes an everting catheter which is capable of dilation and preferably a dilatation everting catheter, i.e. an everting catheter having a dilatation everting element and an endoscope. Dilatation everting catheters are known and are, for example, shown in Fogarty et al U.S. Pat. No. 4,271,839.

The everting catheter and the endoscope are advanced to a position adjacent the site of a stenosis in an internal tubal passage of a patient. The everting catheter includes an endoscope lumen, and the endoscope is within the endoscope lumen. In the case of a partial occlusion, the everting element is everted to a location within the stenosis, and the everting element is then expanded to reduce the stenosis. In the case of a total occlusion, the everting element may be everted to pierce an opening into or through the stenosis and then the everting element is expanded radially to reduce the stenosis. Regardless of how the everting element is advanced into the stenosis, it is used to reduce the stenosis. Thereafter, the everting element is retracted from such location.

The endoscope is used to view the site of the stenosis. This viewing may include viewing the stenosis before and/or after the everting element is expanded to reduce the stenosis. By viewing the stenosis prior to dilatation, the physician can better assess the nature of the stenosis, and by viewing of the site of the stenosis following dilatation, the success of the procedure can be evaluated. The procedure can also be visually evaluated during the time the procedure is being carried out.

The everting catheter includes an outer catheter having an outer catheter lumen, an inner catheter movable in the outer catheter lumen and having an inner catheter lumen and an everting element coupled to the outer and inner catheters. The endoscope lumen may be in any of several different locations of the catheter. For example, the endoscope lumen may include the inner catheter lumen. Alternatively, the endoscope lumen may include the outer catheter lumen, and in this event the step of viewing is carried out with the endoscope through the everting element. In order to accomplish viewing through the everting element, the everting element must be transparent to the wavelengths of interest. Another alternative is for the catheter to include an endoscope lumen which is outside of the outer catheter lumen. The everting catheters used in the latter two alternatives in which the endoscope is out of the inner catheter lumen need not be capable of dilatation if they are not to be used for dilatation.

When the method of this invention employs an endoscope in the inner catheter lumen, the everting element when inflated grips the endoscope and can be used to advance and retract the endoscope. In order to axially position the endoscope, it may be necessary to remove this gripping force from the endoscope so that the endoscope can be freely moved relative to the everting element. Although this could be accomplished by deflating the everting element, preferably it is carried out by introducing a flush solution between the everting element and the endoscope where the everting element grips the endoscope. This removes the gripping force sufficiently so that the endoscope can be moved relative to the everting element while the flush solution is between the everting element and the endoscope. This flush solution also has the advantage of clearing debris from the field of view, helps keep the lens of the endoscope clear and distends tissue at the distal end of the everting element to further assist viewing. This technique is described more specifically in common assignee's copending parent application Ser. No. 780,871 filed on Oct. 18, 1991.

A catheter system and method in which the endoscope lumen includes the outer catheter lumen have the advantage that the endoscope is isolated by the outer and inner catheters and the everting element so that it is more difficult to unintentionally injure the patient with the endoscope. The endoscope is also held out of contact with the patient to protect the patient from any sterilization residuals that may exist on the endoscope. Finally, with this construction, the inner catheter lumen is not obstructed by the endoscope and is left open for other purposes such as delivery of fluids, members or substances.

A catheter system and method in which the endoscope lumen is outside the outer catheter lumen provides some of the same advantages. Thus, with this construction, the inner catheter lumen is not obstructed by the endoscope and the endoscope can be retained entirely within the endoscope lumen, if desired. In this embodiment, the endoscope may be permanently retained in a fixed position within the endoscope lumen, but it is preferably slidable in the endoscope lumen to various axial positions and removable from the endoscope lumen. If the endoscope is removable from the catheter, it can be reused and the catheter, which is less expensive, can be disposable.

The method of this invention as well as the catheter system of this invention can be utilized for tubal recanalization of various internal tubal passages of a patient including those examples of internal tubal passages given above. However, they are particularly adapted for use either in the vascular system, the fallopian tubes or the cervical canal. In the fallopian tubes, the stenosis may include mucous, fibrotic material or adhesions in strand-like form. Because this invention does not require the use of X-rays, it is particularly adapted for use in treating and assessing a stenosis in a fallopian tube.

The invention, together with additional features and advantages thereof may best be understood by reference to the following description taken in connection with the accompanying illustrative drawings.

BRIEF DESCRIPTION OF THE DRAWINGS

FIG. 1 is an elevational view of an everting catheter which can be used in carrying out the method of this invention. The everting element is inverted.

FIG. 2 is an elevational view partially in section of an endoscope which can be used with the everting catheter to carry out the method of this invention.

FIG. 3 is an enlarged, fragmentary, axial sectional view of a distal region of the everting catheter and endoscope with the everting element partially everted.

FIG. 3A is a view similar to FIG. 3 showing a preferred way to move the endoscope relative to the everting element.

FIGS. 4–7 are viewed similar to FIG. 3 illustrating the steps in carrying out the dilatation-evaluation procedures of this invention.

FIG. 8 is a sectional view similar to FIG. 3 illustrating one way to utilize the endoscope in the outer catheter lumen.

FIG. 9 is a section view similar to FIG. 3 illustrating one way of providing an endoscope lumen which is outside the outer catheter lumen.

DESCRIPTION OF THE PREFERRED EMBODIMENTS

FIG. 1 shows an everting catheter 11 which is capable of dilatation. Preferably the catheter 11 is a dilatation everting catheter, i.e. an everting catheter which is adapted for dilatation. For example, the everting catheter 11 may be of the type which is adapted for accessing of the vascular system to treat a stenosis in the vascular system or of a type adapted for accessing the fallopian tubes for treating a stenosis in the fallopian tubes or of a type for treating a stenosis in the cervical canal or for treating a stenosis in any other internal tubal passage. Dilatation everting catheters are known, and if desired the everting catheter 11 may be of a known design. The everting catheter 11 generally comprises an outer catheter 13, an inner catheter 15 and an everting element 17 (FIG. 3). The outer catheter 13 includes an elongated, flexible catheter body 19 and an outer catheter fitting 21 coupled to the proximal end of the catheter body 19. The outer catheter 13 has an outer catheter lumen 23 (FIG. 3) which extends for the full length of the catheter body 19 and opens at a distal opening 25 (FIG. 3). The distal opening 25 need not be at the distal end of the catheter body 19.

A dilatation everting catheter is distinguished from other everting catheters by the characteristics of the everting element. Generally, a dilatation everting catheter is characterized by expansion to a predicable, known diameter when inflated and added strength to withstand the dilatation pressures necessary to expand the everting element and to reduce or compress a stenosis. Generally, a dilatation everting element is expandable with relative ease to the predicted, known diameter and thereafter provides significantly increased resistance to further expansion even in the presence of increased internal pressure.

The catheter body 19 has a distal end portion 27 which, in its unstressed condition, may be straight or of any other shape designed to best gain access to the internal tubal passage of interest. Although the distal end portion 27 is illustrated as being straight, it may be curved and form a portion of a circular arc in the unstressed condition to facilitate access to the ostia of fallopian tubes. Alternatively, the distal end portion 27 may be configured to facilitate gaining access to a desired region of the vascular system. The shape of the distal end portion 27 may be linear, and because it forms no part of this invention, it is shown for convenience as being linear.

The outer catheter 13 may be of conventional construction, and the catheter body 19 may be constructed of a flexible, biocompatible polymeric material. The outer catheter fitting 21 has an injection leg 29 which is coupled to an inflation media source 31 for providing inflation media under pressure to the outer catheter lumen 23 to control the inversion and eversion of the everting element 17 as well as the dilatation of the everting element in a known manner. The inflation media source 31 can be any known, or suitable, means for delivering inflation media under a suitable pressure to the everting element 17, such as a syringe or pump. The inflation media may be, for example, water or a contrast dye.

The inner catheter 15 is extendible through the outer catheter fitting 21 and is movable longitudinally in the outer catheter lumen 23. The inner catheter 15 also includes an elongated, flexible catheter body 33 of a suitable polymeric material and an inner catheter fitting 35. The inner catheter fitting 35 has a leg 37 which is coupled to a pressurized irrigation source 39 which provides flush solution under pressure and on demand through the inner catheter fitting 35 to an inner catheter lumen 41 (FIG. 3). The inner catheter lumen 41 extends axially for the full length of the inner catheter body 33 and opens at a distal opening 43 (FIG. 3) at a distal end 45 of the inner catheter body 33. Although the pressurized irrigation source 39 can take different forms as mentioned above, in this embodiment it is a peristaltic or syringe pump. Similarly, although there are a variety of flush solutions that can be used, in this embodiment the flush solution is a saline type solution.

The everting element 17 is a thin, flexible membrane which is constructed of a suitable polymeric material. The everting element 17 is bonded as by a suitable adhesive to the catheter body 19 of the outer catheter 13 closely adjacent the distal opening 25 and to a distal tip region of the catheter body 33 of the inner catheter 15 in accordance with known techniques. This forms a chamber 47 with the catheter body 19. Consequently, inflation media from the source 39 acting in the chamber 47 can bring about inversion and eversion of the everting element 17. The everting element 17 has a distal end 49. The everting element 17 forms a coaxial extension 51 of the inner catheter lumen 41 and they form an endoscope lumen for receiving the endoscope of FIG. 2. In this embodiment, the outer catheter 13 and the inner catheter 15 may be of conventional construction, if desired.

The everting catheter 11 can be used with an endoscope 53 in an everting catheter system to carry out the method of this invention. The endoscope 53, which may be conventional, includes an elongated, flexible body 55 and a hub 57. The endoscope 53 also includes one or more illumination fibers 59 and image visualization fibers 61.

The endoscope body 55 has a proximal end 63 and a distal end 65. The proximal end 63 is received within an axial passage 67 of the hub 57. A strain relief tube 69 receives a region of the endoscope body 55 adjacent the proximal end 63 and the strain relief tube is also received within the passage 67. An adhesive 71, such as urethane adhesive, joins the endoscope body 55 to the tube 69. The endoscope body 55 and tube 69 are affixed to the hub 57 in any suitable manner, such as by a urethane adhesive.

The illumination fibers 59 extend from the distal end 65 through the full length of the endoscope body 55, into the passage 67 and through a leg 73 or illumination connector of the hub 57 which is adapted to be coupled to a light source (not shown). Similarly, the image fibers 61 extend from the distal end 65 through the full length of the endoscope body 55 into the passage 67 and into a leg 75 of the hub 57. A suitable adhesive, such as an epoxy adhesive may be used to bond the ends of the fibers 59 and 61 to the legs 73 and 75, respectively. Although the leg 75 could be adapted for coupling to an eyepiece (not shown) to permit direct visualization, in this embodiment it is adapted for coupling to a camera (not shown) to enable the image to be viewed on a monitor. The endoscope 53 and the inner catheter 15 may have indicia 77 and 79, respectively, which can be used as set forth in Woker et al U.S. Pat. No. 5,163,927 to identify the location of the distal end 65 relative to the distal end 49.

As shown in FIG. 1, the endoscope body 55 extends through the inner catheter fitting 35 into the endoscope lumen, i.e., into the inner catheter lumen 41 and the everting element 17 (FIG. 3). The endoscope 53 can move both proximally and distally relative to the inner catheter 15. The everting catheter system which comprises the everting catheter 11 and the endoscope 53 are utilized for tubal recanalization of an internal tubal passage of a patient. FIGS. 4–7 show a tubal passage 81 of a patient which may be considered as either a fallopian tube or a portion of the vascular system, such as an artery. The tubal passage has a stenosis 83 which partially occludes the tubal passage 81.

In carrying out the method of this invention, the catheter body 19, either with or without the endoscope is advanced to a position adjacent the site of the stenosis 83 in the internal tubal passage 81 of the patient. Preferably, the catheter body 19 and the endoscope 53 are advanced together to this position so that the endoscope can be used to provide visual information during the advancing movement of the catheter body 19. If the tubal passage 81 is in the vascular system, access to the vascular system can be obtained in any known manner for dilatation catheters. If the tubal passage 81 is a fallopian tube, then the catheter body 19 is inserted through the cervix and uterus into the fallopian tube in accordance with known techniques. Typically, the everting element 17 is inverted during at least the initial portion of the advancing movement of the catheter and everted into the fallopian tube with the distal opening 25 of the catheter body at or hear the ostium of the fallopian tube.

Next, inflation media from the source 31 is introduced through the outer catheter fitting 21 and the outer catheter lumen 23 to the chamber 47. This causes the everting element 17 to grip the endoscope 53 as shown by way of example in FIG. 3 and causes the everting element to evert or evert farther. In the case of an artery, the eversion occurs within the artery, and in the case of a fallopian tube, the eversion may begin at an ostium and occur into the fallopian tube.

It can be seen in FIG. 3 that the everting element 17 grips a region 85 of the endoscope 53. Because the endoscope 53 is gripped by the everting element 17 as the everting element everts, the everting element also pulls the endoscope along in the tubal passage 81. This gripping of the region 85 of the endoscope 53 by the everting element 17 prevents, or substantially prevents, moving of the endoscope 53 relative to the everting element, and in particular, it prevents relative longitudinal movement of the endoscope and the everting element.

In order to position the endoscope 53 as desired in the tubal passage 81, it is necessary to move the endoscope independently of the everting element 17. Although this can be accomplished in various was such as by deflating of the everting element 17, preferably this is accomplished utilizing flush solution from the irrigation source 39. This flush solution is introduced through the inner catheter fitting 35 and the inner catheter lumen 41 and between the everting element 17 and the endoscope 53 where the everting element grips the endoscope, i.e. at the region 85. The flush solution lubricates the interface between the everting element 17 and the endoscope 53 at the region 85 and may form a layer of flush solution for the full length of the region 85 and completely circumferentially around the region 85. As such, this flush solution separates the everting element 17 and the endoscope 53 at the region 85. The flush solution preferably flows completely through the region 85 and exits out the distal end 49 of the everting element 17 as shown in FIG. 3A. Because the flush solution between the everting element 17 and the endoscope 53 in the region 85 separates the everting element and the endoscope as shown in FIG. 3A, the endoscope can be moved relative to the everting element. Such movement of the endoscope 53 may be rotational and/or longitudinal but typically is longitudinal so as to more desirably position the distal end 65 of the endoscope for viewing the site of the stenosis 83.

In order to obtain the flow of flush solution between the everting element 17 and the endoscope 53 at the region 85, the pressure of the flush solution from the irrigation source 39 is preferably greater than the pressure of the inflation media in the chamber 47. For example, if the inflation media is at 4 atmospheres, the pressure of the flush solution provided by the irrigation source 39 may be slightly above 4 atmospheres.

As shown, for example, in FIGS. 3 and 4–7, the inflated everting element 17 radially positions, and more specifically centers, the endoscope 53 in the outer catheter lumen 23 and in the tubal passage 81. Preferably, the introduction of the flush solution to and through the region 85 is carried out with the everting element 17 continuing to perform its radial positioning or centering function. To best accomplish this, the steps of introducing the flush solution to and through the region 85 and the movement of the endoscope are preferably carried out without reducing the pressure of the inflation media in the chamber 47.

The catheter system has sufficient compliance to allow movement of the everting element 17 off of the endoscope 53 in the region 85. Such compliance may be afforded, for example, by the everting element 17, the catheter body 19 and any tubing coupling the outer catheter fitting 21 to the inflation media source 31. When the introduction of the flush solution is terminated, the inflation media pressure within the chamber 47 again forces the everting element to grip the endoscope 53. The length of the endoscope 53 which is gripped depends upon the extent to which the everting element 17 is everted. The flush solution from the source 39 may be pulsed, intermittent or applied under steady state conditions. Utilizing this technique, the endoscope 53 can be advanced relative to the everting element 17 from the position of FIG. 4 to the position of FIG. 5. As shown in FIG. 5, the endoscope 53 can be used to view the stenosis 83 and make a pre-procedure evaluation of the stenosis.

Thereafter, the everting element 17 is advanced into or through the stenosis 83. If the stenosis 83 completely occludes the passage 81, the stenosis is first pierced in any suitable manner such as by everting the everting element 17 axially into or through the stenosis. The everting element 17 is then expanded by increasing the pressure in the chamber 47 as shown in FIG. 6 to compact and reduce the stenosis 83. During this time, the endoscope 53 may be within or through the stenosis 83 as illustrated in FIG. 6 or retracted from the stenosis toward the outer catheter body 19. Upon completion of the procedure, the everting element 17 is retracted out of the site of the stenosis 83 by partially inverting the everting element 17. The endoscope 53 is positioned so that its distal end 65 is at or near the distal end 49 of the everting element 17 proximally of the site of the stenosis 83 so that a post procedure visualization and analysis of the site of the stenosis can be made utilizing the endoscope. Thereafter, the catheter 11 and the endoscope 53 are withdrawn from the tubal passage 81.

FIG. 8 shows an everting catheter system 101 which may also be used in the method of this invention. The everting catheter system 101 includes an everting catheter 11a and an endoscope 53a. The everting catheter 11a may be identical to the everting catheter 11 and portions of the catheter 11a corresponding to portions of the catheter 11 are designated by corresponding reference numerals followed by the letter "a". Similarly, the endoscope 53a may be identical to the endoscope 53 and portions of the endoscope 53a corresponding to portions of the endoscope 53 are designated by corresponding reference numerals followed by the letter "a".

The primary difference between the embodiment of FIG. 8 and the embodiment of FIGS. 1–3 is that the endoscope lumen includes the outer catheter lumen 23a and the chamber 47a and the endoscope 53a is located in the outer catheter lumen, and if desired in the chamber 47. Consequently, viewing is carried out with the endoscope 53a through the everting element 17a.

In order to permit viewing through the everting element 17a, at least a region of the everting element must be sufficiently transparent to permit visualization through such region. This, however, may or may not differentiate the everting catheter system 101 from the embodiment of FIGS. 1–3 in that the everting element 17 of the embodiment of FIGS. 1–3 may also be transparent, if desired.

The axial position of the endoscope 53a in the outer catheter lumen 23a can be adjusted. Preferably a distal region of the endoscope 53a and the distal end 65a of the endoscope are within the everting element 17a and in the chamber 47a with the distal end 65a of the endoscope closely adjacent the distal end 49a of the everting element 17a.

FIG. 9 shows an everting catheter system 201 which may also be used in the method of this invention. The catheter system 201 may be identical to the catheter system of FIGS. 1–3 except as shown or described herein. Portions of the everting catheter system 201 corresponding to portions of the embodiment of FIGS. 1–3 are designated by corresponding reference numerals followed by the letter "b".

The everting catheter system 201 includes an outer catheter 13b which has an outer catheter lumen 23b and an endoscope lumen 203. The primary differences between the everting catheter system 201 and the embodiment of FIGS. 1–3 are the separate endoscope lumen 203 and the placement of the endoscope 53b in the endoscope lumen. The outer catheter lumen 23b and the endoscope lumen 203 are spaced radially, and the endoscope is slidably insertable into the endoscope lumen so it can be inserted and removed from the endoscope lumen. The endoscope lumen 203 has a distal opening 205 which, in the embodiment illustrated, terminates in the same plane as the distal opening 25b of the outer catheter lumen 23b. The lumens 23b and 203 may be coextensive in length. If the endoscope 53b is bonded into the endoscope lumen 203, the distal end 65b of the endoscope preferably terminates substantially at the plane of the distal opening 205.

The catheter systems 101 and 201 can be used in the method of this invention in the same manner as described above in connection with the embodiment of FIGS. 1–3 except that the endoscopes 53a and 53b are not gripped by the associated everting elements 17a and 17b. Consequently, there is no need to utilize flush solution or any other technique to free the endoscope of the catheter systems 101 and 201 for independent movement relative to the associated everting element. Preferably, the endoscope 53a may be moved into the tubal passage along with the everting catheter 11a so the tubal passage can be viewed as the catheter is advanced; however it may be inserted after placement of the catheter. The same is true of the endoscope 53b if the endoscope is not bonded into the endoscope lumen 203. The catheter system 201 is not adapted for use in the fallopian tubes because the endoscope 53b is outside of the everting element 17b which is the portion of the catheter system that is advanced into the fallopian tubes.

Although exemplary embodiments of the invention have been shown and described, many changes, modifications and substitutions may be made by one having ordinary skill in the art without necessarily departing from the spirit and scope of this invention.

We claim:

1. A method of tubal recanalization comprising:
advancing an everting catheter capable of dilatation and an endoscope to a position adjacent the site of a stenosis in an internal tubal passage of a patient, said everting catheter including an endoscope lumen receiving the endoscope and an everting element which is inflatable to grip the endoscope;
everting the everting element to a location within the stenosis;
expanding the everting element to reduce the stenosis;
retracting the everting element from said location;
viewing said site using the endoscope; and
introducing a solution between the everting element and the endoscope where the everting element grips the endoscope, and moving the endoscope relative to the everting element while the solution is between the everting element and the endoscope to position the endoscope.

2. A method as defined in claim 1 wherein the step of viewing includes viewing the stenosis using the endoscope prior to said step of expanding.

3. A method as defined in claim 1 wherein said step of viewing is used to locate said site.

4. A method as defined in claim 1 wherein the step of viewing includes viewing said site using the endoscope after said step of retracting.

5. A method as defined in claim 4 wherein the step of viewing includes viewing the stenosis using the endoscope prior to said step of expanding.

6. A method as defined in claim 1 wherein the everting catheter includes an outer catheter having an outer catheter lumen and an inner catheter movable in the outer catheter lumen, and having an inner catheter lumen, the everting element is coupled to the outer and inner catheters and the endoscope lumen includes said inner catheter lumen.

7. A method as defined in claim 1 wherein the internal tubal passage is a fallopian tube.

8. A method as defined in claim 7 wherein the step of viewing includes viewing the stenosis using the endoscope prior to said step of expanding and viewing said site using the endoscope after said step of retracting.

9. A method as defined in claim 7 wherein the step of viewing includes viewing the stenosis using the endoscope prior to said step of expanding.

10. A method as defined in claim 7 wherein said step of viewing is used to locate said site.

11. A method as defined in claim 7 wherein the step of viewing includes viewing said site using the endoscope after said step of retracting.

12. A method as defined in claim 1 wherein the internal tubal passage is in the vascular system.

13. A method as defined in claim 1 wherein the internal tubal passage is the cervical canal.

14. A method as defined in claim 1 wherein said step of moving is carried out before said step of everting.

15. A method as defined in claim 1 wherein the everting element and the endoscope have distal ends and the step of moving includes moving the distal end of the endoscope longitudinally relative to the distal end of the everting element.

16. A method of tubal recanalization comprising:
advancing an everting catheter capable of dilatation and an endoscope to a position adjacent the site of a stenosis in an internal tubal passage of a patient, said everting catheter including an outer catheter having an outer catheter lumen, an inner catheter movable in the outer catheter lumen and having an inner catheter lumen, an everting element coupled to the outer and inner catheters and an endoscope lumen which includes the outer catheter lumen, the endoscope being within the endoscope lumen;
everting the everting element to a location within the stenosis;
expanding the everting element to reduce the stenosis;
retracting the everting element from said location; and
viewing said site through the everting element using the endoscope.

17. A method of tubal recanalization comprising:
advancing an everting catheter capable of dilatation and an endoscope to a position adjacent the site of a stenosis in an internal tubal passage of a patient, said everting catheter including an outer catheter having an outer catheter lumen, an inner catheter movable in the outer catheter lumen and having an inner catheter lumen, an everting element coupled to the outer and inner catheters and an endoscope lumen outside the outer catheter lumen, the endoscope being within the endoscope lumen;
everting the everting element to a location within the stenosis;
expanding the everting element to reduce the stenosis;
retracting the everting element from said location; and
viewing said site using the endoscope.

18. A method of tubal recanalization comprising:
advancing an everting catheter capable of dilatation and an endoscope to a position adjacent the site of a stenosis in an internal tubal passage of a patient, said everting catheter including an endoscope lumen receiving the endoscope and an everting element which is inflatable to grip the endoscope;
everting the everting element to a location within the stenosis;
expanding the everting element to reduce the stenosis;
retracting the everting element from said location;
viewing said site using the endoscope; and
introducing a solution between the everting element and the endoscope where the everting element grips the endoscope to assist the viewing of said site.

19. A method as defined in claim 18 wherein the internal tubal passage is a fallopian tube.

20. A method of tubal recanalization comprising:

advancing an everting catheter capable of dilatation and an endoscope to a position adjacent the site of a stenosis in a fallopian tube of a patient, said everting catheter including an endoscope lumen receiving the endoscope and an everting element which is inflatable to grip the endoscope;

everting the everting element to a location within the stenosis;

expanding the everting element to reduce the stenosis;

retracting the everting element from said location;

viewing said site using the endoscope; and introducing a solution between the everting element and the endoscope where the everting element grips the endoscope, and moving the endoscope longitudinally relative to the everting element while the solution is between the everting element and the endoscope to position the endoscope.

* * * * *